United States Patent [19]
Bally et al.

[11] Patent Number: 4,668,186
[45] Date of Patent: May 26, 1987

[54] APPARATUS FOR DISPENSING ELASTIC BANDS AND ASSOCIATED METHOD

[75] Inventors: Alex Bally, Carnegie; Charles Kraeuter, West Mifflin, both of Pa.

[73] Assignee: The Bally Orthodontics Group, Carnegie, Pa.

[21] Appl. No.: 702,037

[22] Filed: Feb. 15, 1985

Related U.S. Application Data

[63] Continuation-in-part of Ser. No. 585,329, Mar. 1, 1984, abandoned.

[51] Int. Cl.⁴ .............................................. A61C 7/00
[52] U.S. Cl. ......................................................... 433/3
[58] Field of Search ............................... 433/3, 11, 18; 221/312 A

[56] References Cited

U.S. PATENT DOCUMENTS

| | | | |
|---|---|---|---|
| 3,330,038 | 7/1967 | Berman | 32/14 |
| 3,547,124 | 12/1970 | Fergusson | 128/303 |
| 3,861,045 | 1/1975 | Canter et al. | 32/66 |
| 3,911,923 | 10/1975 | Yoon | 128/303 A |
| 3,967,625 | 7/1976 | Yoon | 128/326 |
| 4,040,187 | 8/1977 | Cardena | 433/3 |
| 4,127,940 | 12/1978 | Shilliday | 32/66 |
| 4,257,420 | 3/1981 | Terayama | 128/303 A |
| 4,277,236 | 7/1981 | Kurz | 433/3 |
| 4,472,137 | 9/1984 | Barone | 433/3 |

Primary Examiner—Robert Peshock
Attorney, Agent, or Firm—Arnold B. Silverman

[57] ABSTRACT

Apparatus and an associated method for effecting dispensing of elastic bands. An elongated handle member cooperates with a slide member which is secured for relative longitudinal sliding movement with respect to the handle. A magazine of the elastic bands is secured to the handle and is adapted to generally forwardly discharge the elastic bands. A pusher member is pivotally mounted on a slide member and is adapted to insert a blade behind the forwardmost elastic band after which forward movement of the slide serves to urge the elastic band away from the remaining elastic bands and to cause it to be expanded radially over the uniquely configurated head portion of the magazine. In a preferred embodiment a cam and cam follower combination cause the pusher member to rotate through its cycle of operation. The first biasing element tends to urge the pusher member into elastic band engaging position and second biasing means tends to urge the elastic bands forwardly. In one preferred embodiment the pusher member is manually engaged and urged forwardly. In another preferred embodiment a rearwardly disposed slide extension may be manually engaged and urged forwardly. The magazine head preferably has a forwardly diverging head portion disposed behind a forwardly converging head portion and terminates in a face portion. In a preferred use, the face portion may be adapted to engage an orthodontic bracket. A magazine having the above-described unique configuration. A method of dispensing elastic bands exemplified by the use of the above-described apparatus.

43 Claims, 70 Drawing Figures

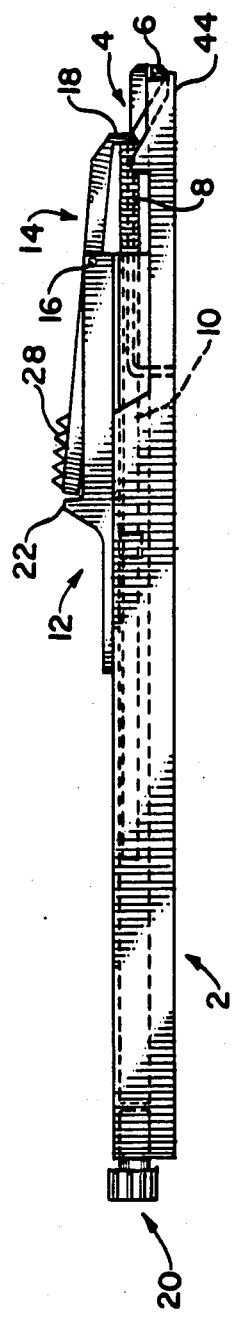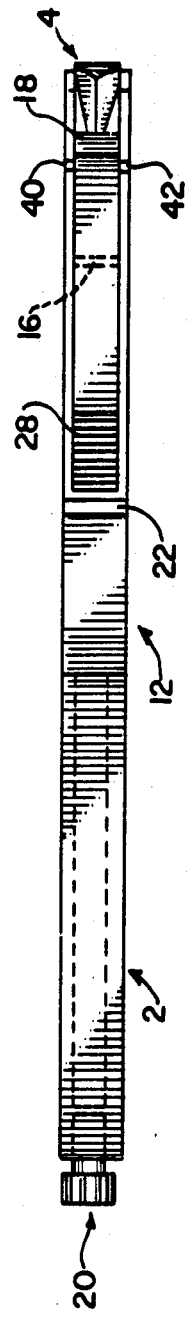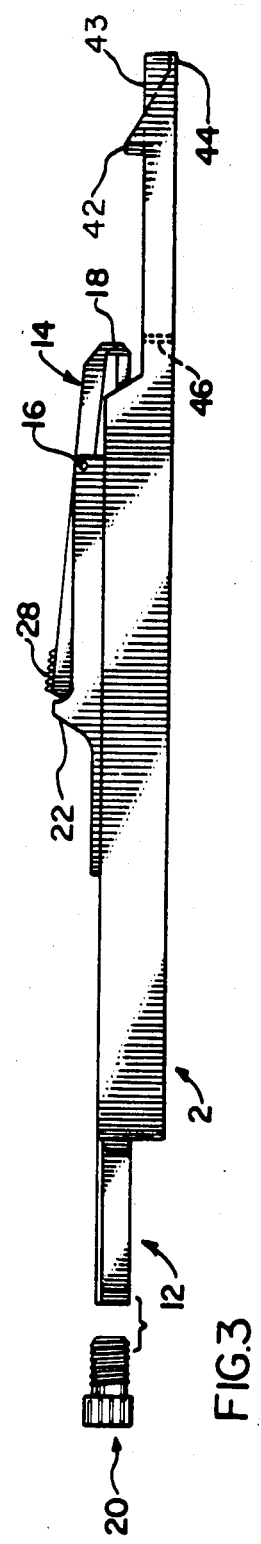

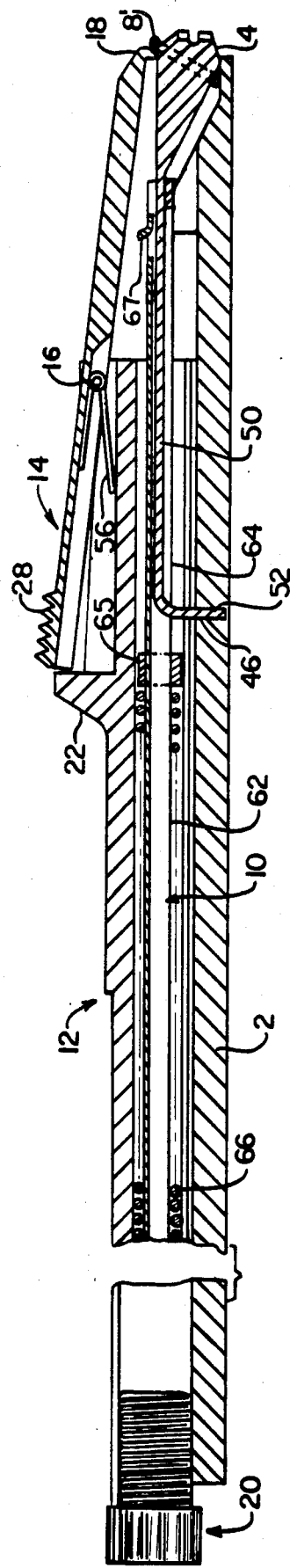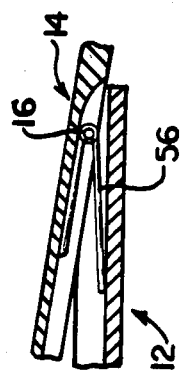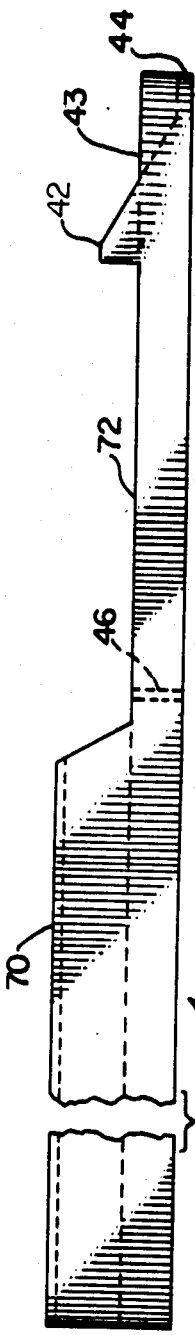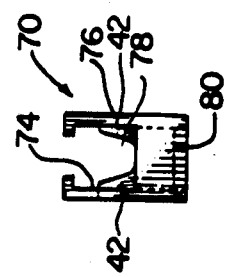
FIG. 4
FIG. 4a
FIG. 5
FIG. 6

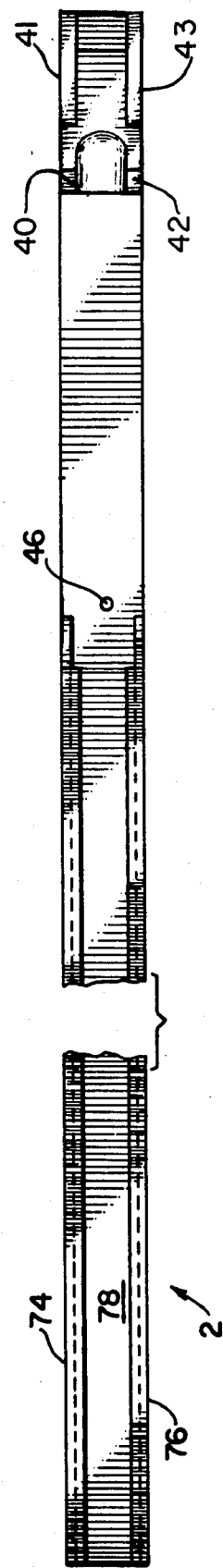
FIG. 7
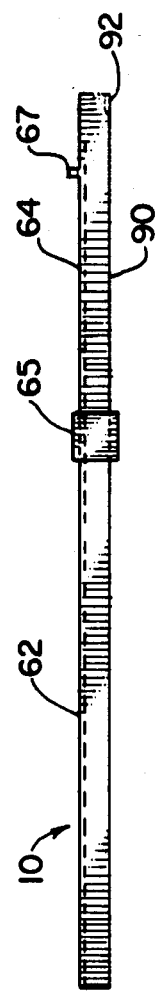
FIG. 8
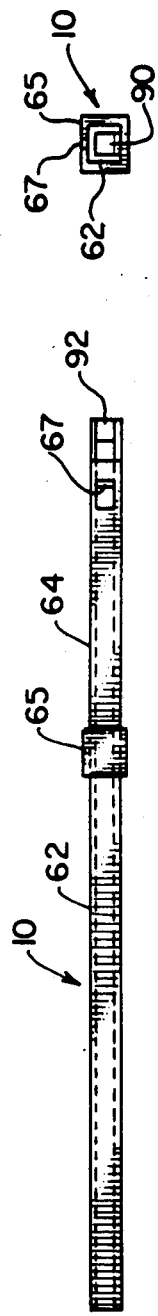
FIG. 10
FIG. 9

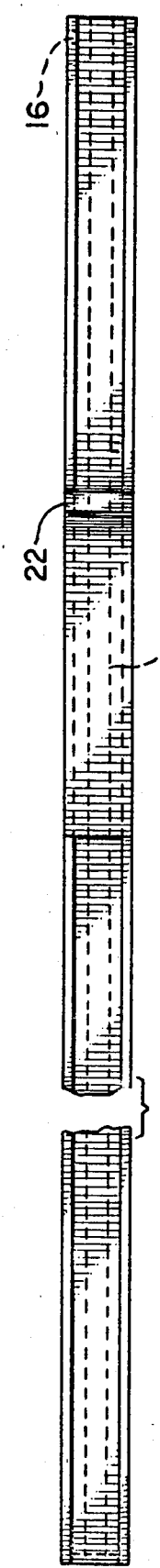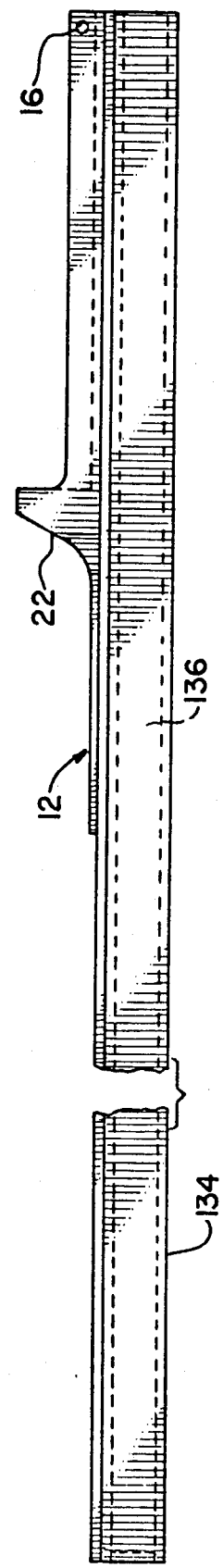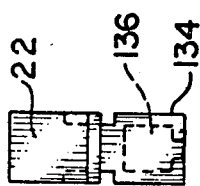
FIG. 20
FIG. 21
FIG. 22

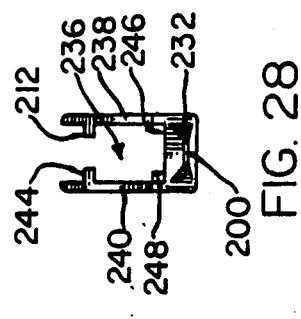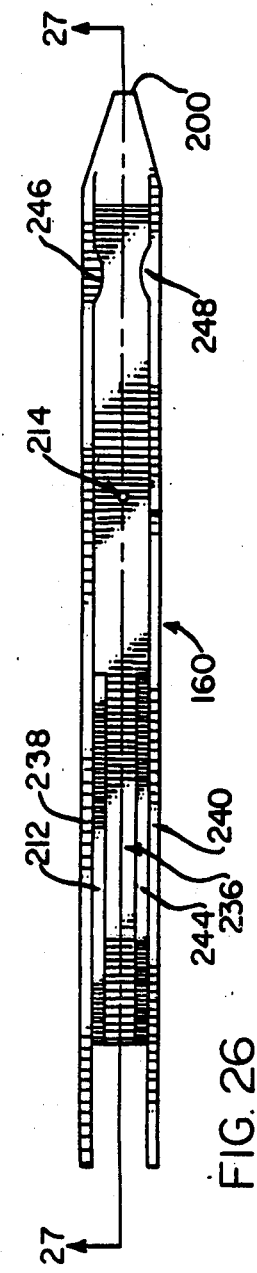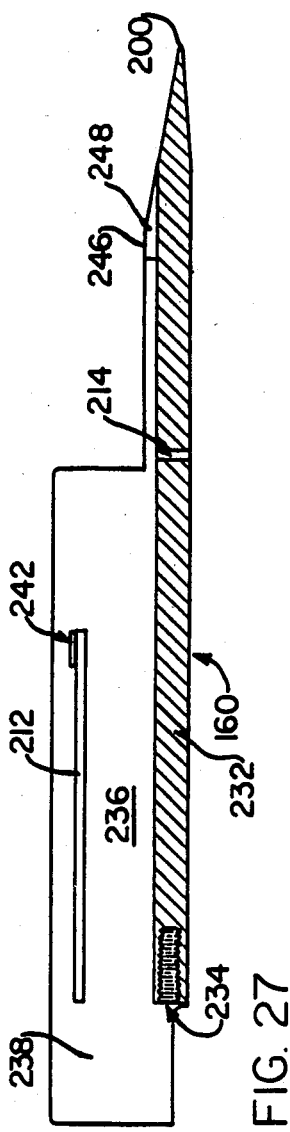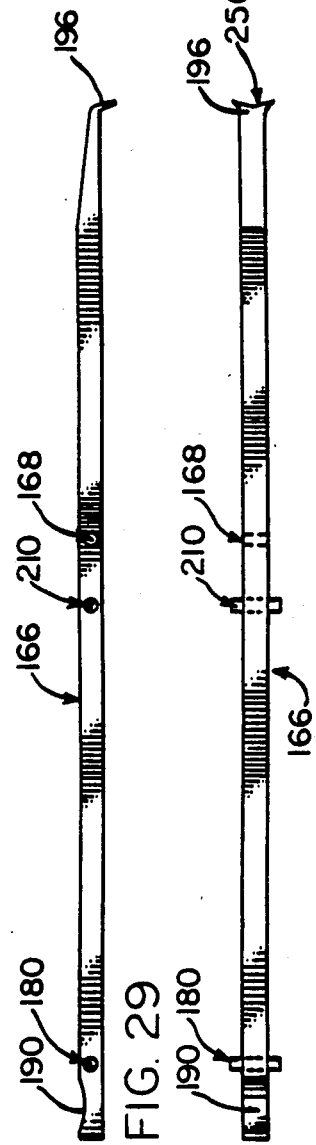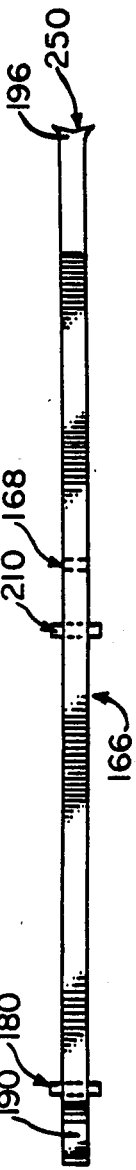

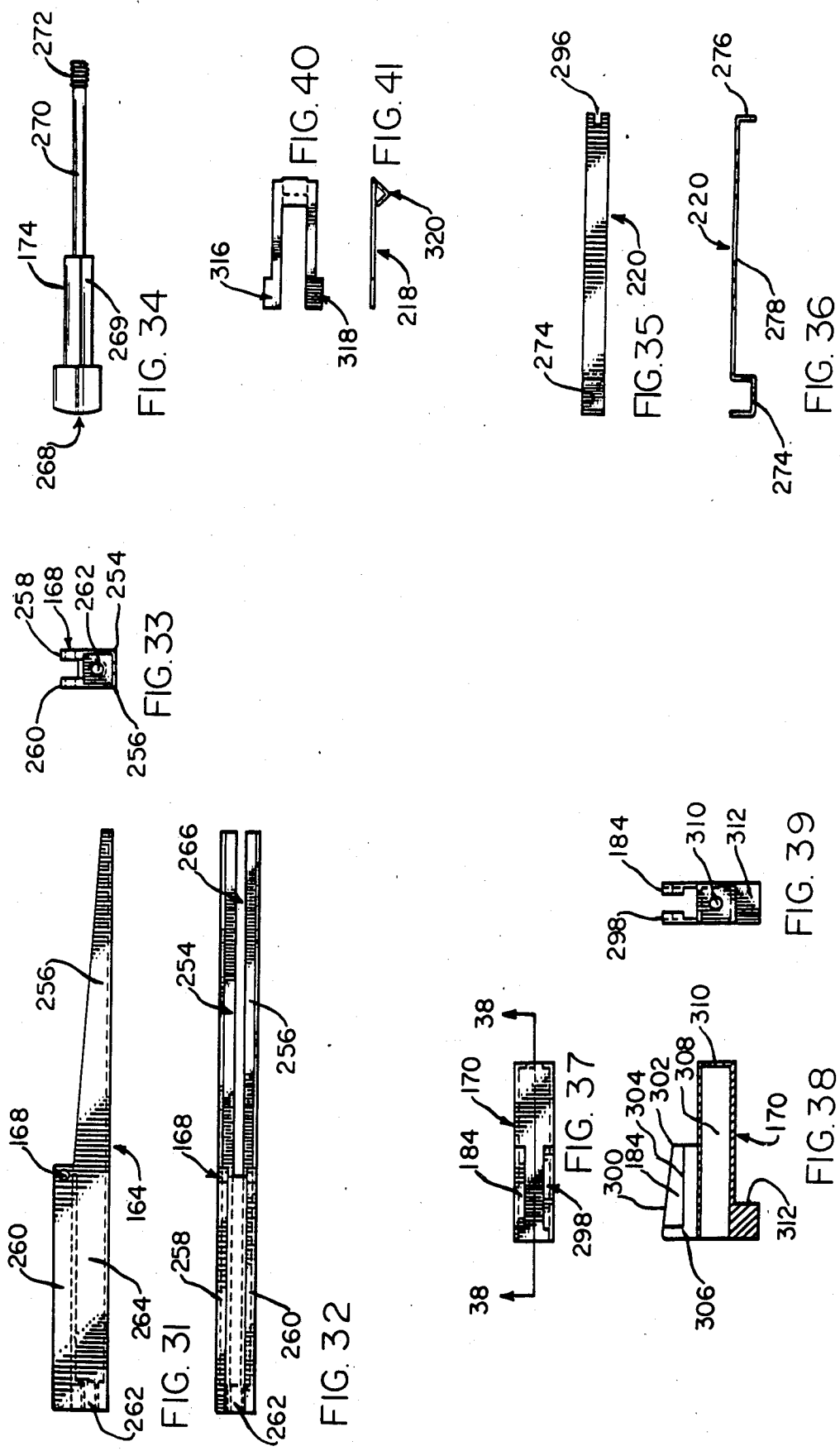

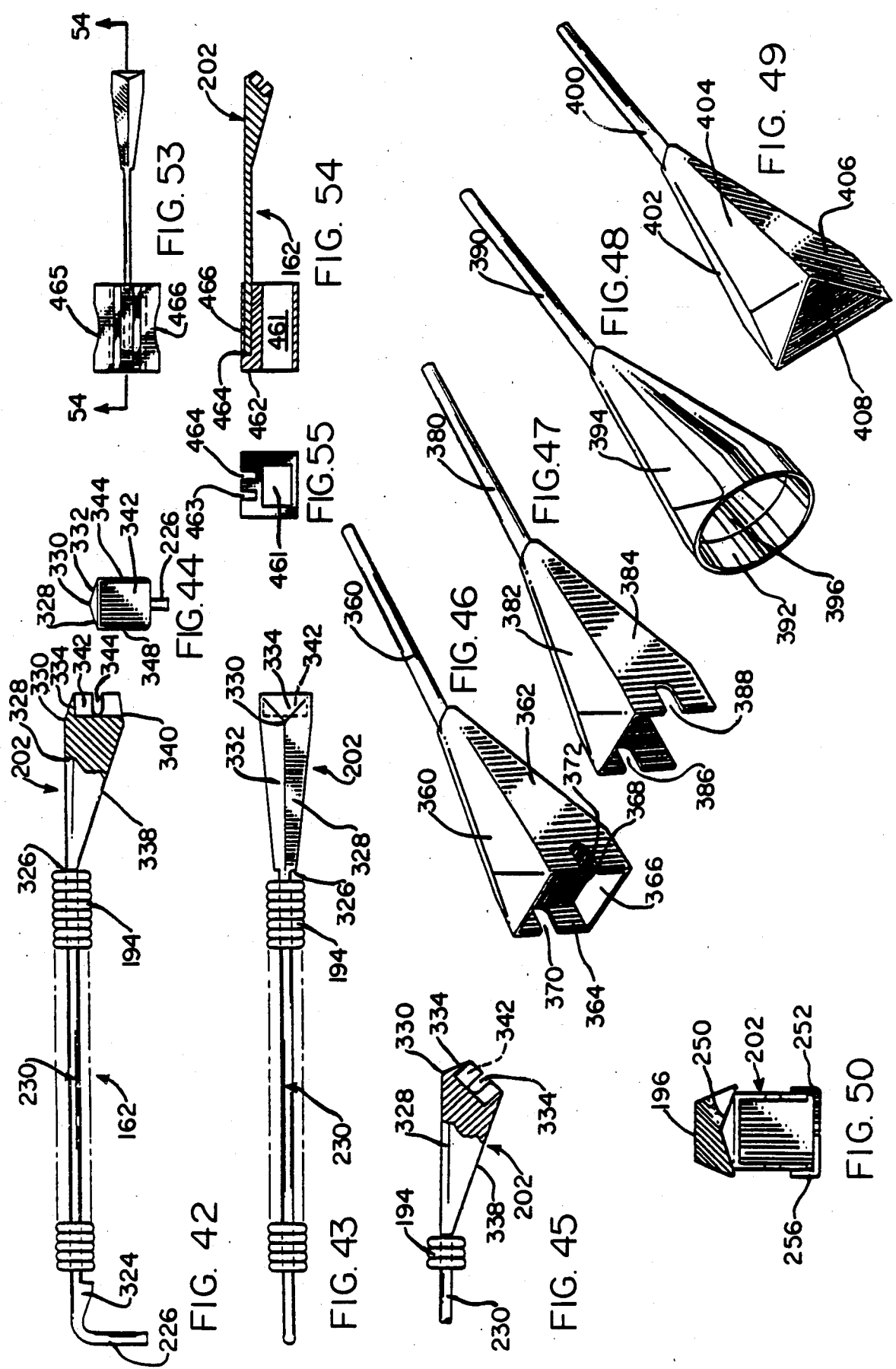

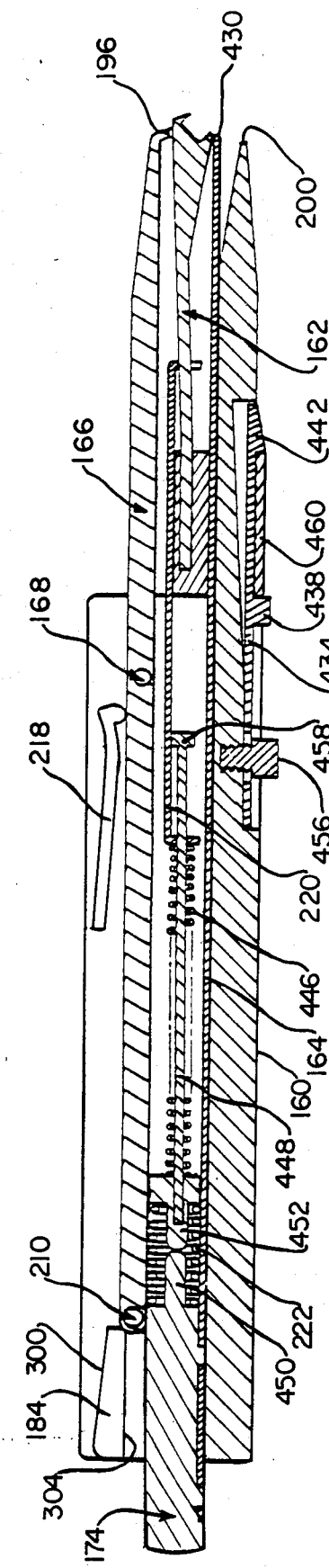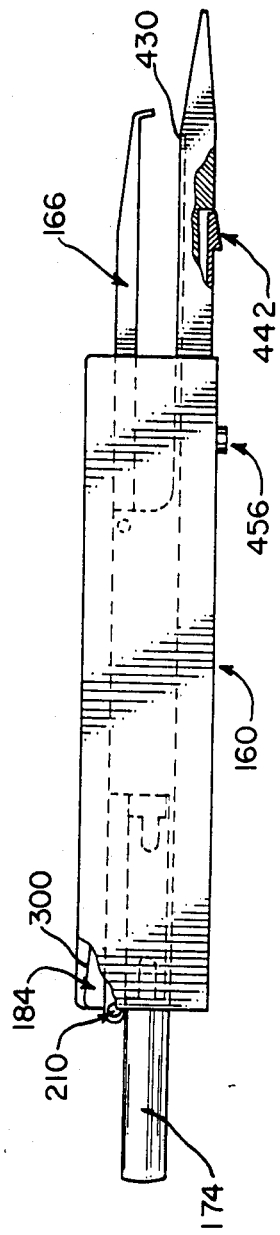
FIG. 51
FIG. 52

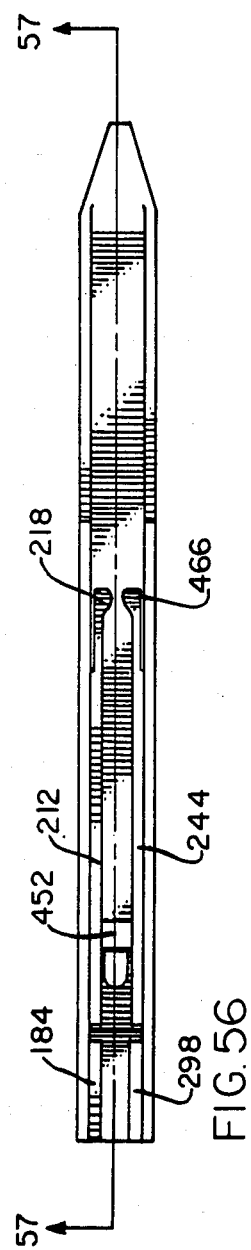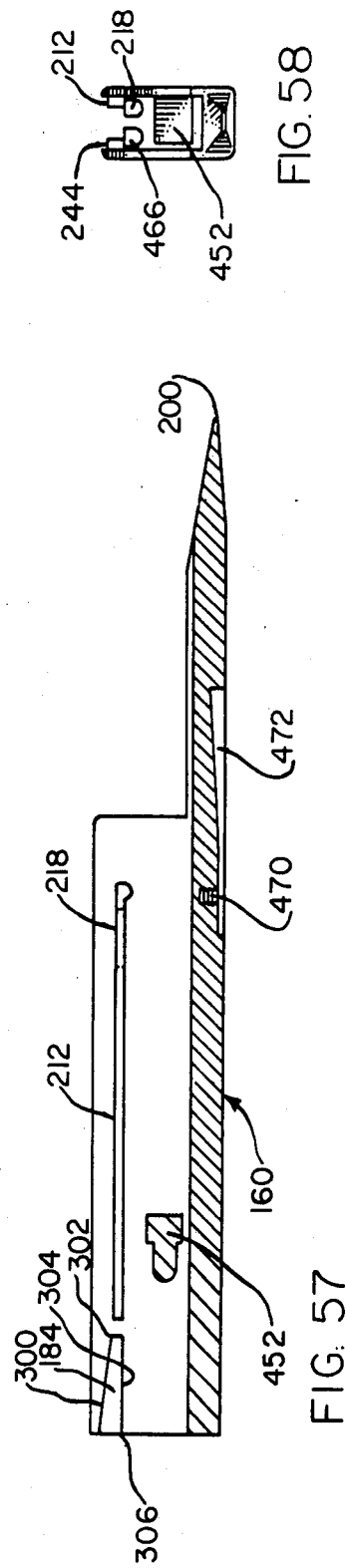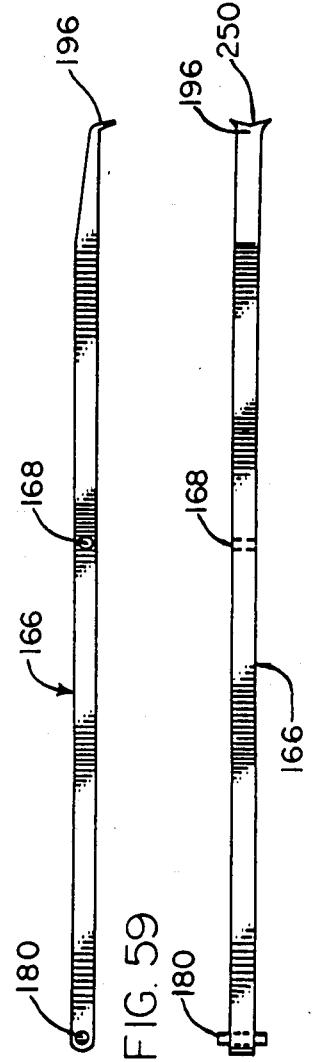

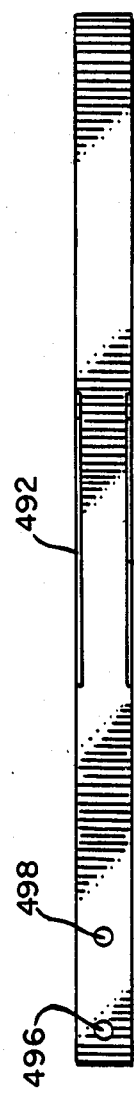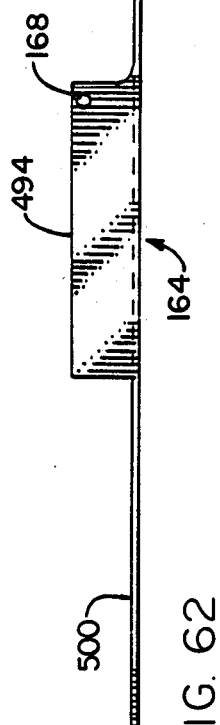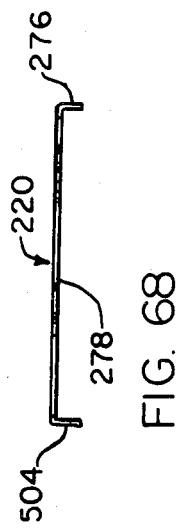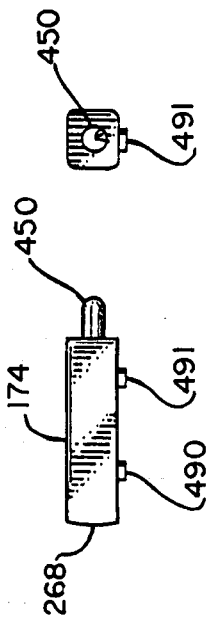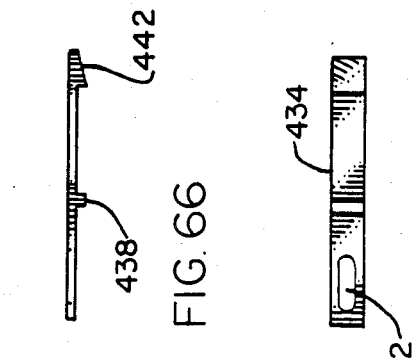

APPARATUS FOR DISPENSING ELASTIC BANDS AND ASSOCIATED METHOD

CROSS REFERENCE TO RELATED APPLICATION

This application is a continuation-in-part of U.S. application Ser. No. 585,329, filed Mar. 1, 1984 and entitled "Apparatus for Dispensing Elastic Band and Associated Method" and now abandoned.

BACKGROUND OF THE INVENTION

1. Field of the Invention

The present invention relates to a unique apparatus and associated method for dispensing in a rapid and efficient manner elastic bands such as are used in connection with orthodontic appliances.

2. Description of the Prior Art

In connection with the use of orthodontics to establish desired movement of teeth, it has been known to secure individual or twin brackets to a patient's teeth and to pass a preshaped arch wire around the exterior of the brackets with the wire being partially received within outwardly open recesses of the bracket. It has been known to employ very small elastic bands which may have an inside diameter of about 1 millimeter and an external diameter of about 2.5 millimeters with a thickness of about 0.8 millimeters, for example, over the brackets in order to secure the wire in place.

Traditionally, the use of such miniature rubber bands or bands made of other materials has been difficult as a result of the small dimensions, the limited access to the work area and the difficulty in securing them to the irregularly configurated clips. It has been known to use tweezers, a hemostat or a small-tipped cleoid scaler for such purposes.

It has also been known to provide such bands on a spine type support which may be used for securing the bands without employing tools.

The prior art practice as hereinbefore described has resulted in the elastics frequently slipping off during installation, the pace of work being slowed by the need to apply them individually and also may, where extreme difficulty is encountered, serve to cast doubt in the mind of the patient upon the orthodontist's competence.

It has been known in other environments to suggest improved devices for the handling of rubber bands for different purposes. See, for example, U.S. Pat. Nos. 3,967,625 and 4,257,420.

U.S. Pat. No. 3,330,038 discloses a color-coded system for facilitating ready selection of the desired size band.

U.S. Pat. Nos. 3,861,045 and 4,127,940 disclose hand tools adapted to be employed with the individual securement of rubber bands.

U.S. Pat. No. 4,040,187 discloses a system adapted to deliver orthodontic rubber bands by insertion of two semicircular cantilevered members between the bands and then urging the same over an enlarged symmetrical surface.

U.S. Pat. No. 4,277,236 discloses an orthodontic elastic handling tool wherein a plurality of wire members are adapted to pass through the centers of the rubber bands and engage the forwardmost one and ultimately to urge it over a flared trumpet configuration.

U.S. Pat. No. 4,472,137 discloses an instrument for attaching orthodontic elastic bands. The instrument has a number of undesirable features including lack of mechanical control and positioning of the elastic bands. It also requires undesirable application of force to the tooth in order to expel the elastic band.

In spite of these prior disclosures, there remains a need for a means for effectively handling and dispensing automatically small elastic bands, such as those used in connection with orthodontic appliances.

SUMMARY OF THE INVENTION

The present invention has met the above-described need by providing a unique apparatus.

In a preferred embodiment of the present invention, a unique magazine cooperates with the remaining apparatus components to provide an easy to use and economical system and its associated method.

The apparatus of the present invention has an elongated handle member with respect to which a slide member is secured for relative longitudinal movement. A magazine of elastic bands is secured to the handle and adapted for generally forward discharge of the elastic bands. Pusher means for separating the bands and causing them to be dispensed from the magazine are pivotally secured to the slide member. First biasing means urge the pusher member into elastic band engaging position and second biasing means urge the elastic bands forwardly.

The magazine preferably has a guide rod on which the elastic bands are slidingly positioned and a head which has a converging portion and terminates in a uniquely configured face which may consist of a transverse recess adapted for engagement with an orthodontic bracket. The slide member preferably has an upwardly projecting pusher tab to facilitate forward movement of the slide and pusher member as a unit. Rearwardly positioned adjustable stop means serves to limit the rearward movement of the slide means such that precise positioning of the stop means will result in rotation of the blade member into a position between the forwardmost and next adjacent elastic bands on the magazine. The magazine is preferably secured to the handle member and the handle member has a forward stop for both limiting forward movement of the slide and for guiding the magazine.

In one embodiment the apparatus has a slide extension which is pushed forwardly to operate the apparatus. Cam means may be provided to effect desired movement of the pusher means.

A method of the present invention is exemplified by use of the hereinbefore described apparatus.

It is an object of the present invention to provide an economical, efficient and rapid means for the dispensing of elastic bands.

It is a further object of the present invention to provide such apparatus and associated method which will permit a magazine which may be reusable or disposable to be employed in the dispensing of elastic bands for orthodontic uses as well as others.

It is a further object of the present invention to provide such apparatus and method which may readily be employed by individuals who are lacking in any particular manual dexterity or experience related to the use of the equipment.

These and other objects of the invention will be more fully understood from the following description of the invention on reference to the illustrations appended hereto.

BRIEF DESCRIPTION OF THE DRAWINGS

FIG. 1 is a front elevational view of one form of the apparatus of the present invention.

FIG. 2 is a top plan view of the apparatus shown in FIG. 1.

FIG. 3 is an elevational view showing a portion of the apparatus of FIG. 1 in a position suitable for loading a magazine.

FIG. 4 is a cross-sectional front elevational view of the apparatus of FIG. 1.

FIG. 4a is a fragmentary cross-sectional view of a wire spring and a portion of the pusher member.

FIG. 5 is a front elevational view of the handle portion of the invention.

FIG. 6 is a right-hand elevational view of the handle portion of FIG. 5.

FIG. 7 is a top plan view of the handle portion of FIG. 5.

FIG. 8 is a front elevational view of a plunger of the present invention.

FIG. 9 is a top plan view of the plunger of FIG. 8.

FIG. 10 is a left side elevational view of the plunger of FIG. 9.

FIG. 20 is a top plan view of a slide member of the present invention.

FIG. 21 is a front elevational view of the slide member of FIG. 20.

FIG. 22 is a left-hand elevational view of the slide member of FIG. 20.

FIG. 26 is a top plan view of the handle portion of this embodiment.

FIG. 27 is a cross-sectional view of the handle portion of FIG. 26 taken through 27—27.

FIG. 28 is a right-hand elevational view of the handle portion of FIG. 26.

FIG. 29 is a front elevational view of a pusher member of the embodiment of FIG. 23.

FIG. 30 is a top plan view of the pusher member of FIG. 29.

FIG. 31 is a front elevational view of a slide member of the embodiment of FIG. 23.

FIG. 32 is a top plan view of the slide member of FIG. 31.

FIG. 33 is a right-hand elevational view of the slide member of FIG. 31.

FIG. 34 is a front elevational view of a slide extension of the embodiment of FIG. 23.

FIG. 35 is a top plan view of a plunger of the present invention.

FIG. 36 is a front elevational view of the plunger of FIG. 35.

FIG. 37 is a top plan view of a pusher member guide of the present invention.

FIG. 38 is a cross-sectional front elevational view of the pusher member guide of FIG. 37 taken through 38—38.

FIG. 39 is a right-hand elevational view of the pusher member guide of FIG. 37.

FIG. 40 is a top plan view of a leaf spring of the embodiment of FIG. 23.

FIG. 41 is a front elevational view of the leaf spring of FIG. 40.

FIG. 42 is a front elevational view of a modified magazine of the present invention.

FIG. 43 is a top plan view of the magazine of FIG. 42.

FIG. 44 is a right-hand elevational view of the magazine of FIG. 42.

FIG. 45 is a front elevational view of a modified magazine of the present invention.

FIGS. 46 through 49 show perspective views of different shapes of discharge heads adapted for use in the present invention.

FIG. 50 is a right-hand elevational view of the magazine of FIG. 42 with the pusher member and slide member engaged.

FIG. 51 is a cross-sectional front elevational view of another embodiment of the apparatus of the present invention.

FIG. 52 is a front elevational view showing a portion of the apparatus of FIG. 51 in a position suitable for loading a magazine.

FIG. 53 is a top plan view of a type of magazine suitable for loading the apparatus of FIG. 52.

FIG. 54 is a cross-sectional view of the magazine of FIG. 53, taken through 54—54.

FIG. 55 is a left-hand elevational view of the magazine of FIG. 53.

FIG. 56 is a top plan view of a handle of the apparatus of FIG. 51.

FIG. 57 is a cross-sectional front elevational view of the handle of FIG. 56 taken through 57—57.

FIG. 58 is a right-hand elevational view of the handle of FIG. 56.

FIG. 59 is a front elevational view of a pusher member of the apparatus of FIG. 51.

FIG. 60 is a top plan view of the pusher member of FIG. 59. FIG. 61 is a top plan view of a slide of the apparatus of FIG. 51.

FIG. 62 is a front elevational view of the slide of FIG. 61.

FIG. 63 is a right-hand elevational view of the slide of FIG. 61.

FIG. 64 is a front elevational view of a slide extension of the apparatus of FIG. 51.

FIG. 65 is a right-hand elevational view of the slide extension of FIG. 64.

FIG. 66 is a front elevational view of a retaining clip of the apparatus of FIG. 51.

FIG. 67 is a bottom plan view of the retaining clip of FIG. 66.

FIG. 68 is a front elevational view of a plunger of the apparatus of FIG. 51.

FIG. 69 is a top plan view of the plunger of FIG. 68.

DESCRIPTION OF THE PREFERRED EMBODIMENT

Figure 11:
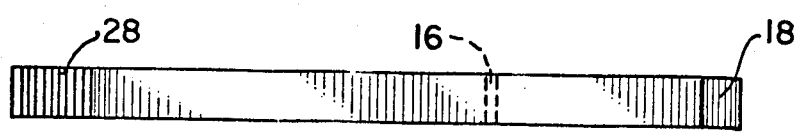
FIG. 11 is a top plan view of a pusher member of the present invention.

Referring now to FIGS. 1 and 2 in greater detail, there is shown an elongated handle member 2 which has secured thereto, in a manner to be described hereinafter, a magazine 4 which has a discharge head 6 disposed forwardly thereon and an array of elastic bands, such as rubber bands 8, for example, through which a guide road passes. A plunger 10 is urged forwardly in order to advance the array of elastic bands 8. Secured in overlying relationship and slidingly movable with respect to the handle 2, is a slide member 12 to which is pivotally secured a pusher 14 which in turn rotates about pivot 16. It will be appreciated that when the pusher is in the form shown in FIG. 1, a depending blade 18 will be interposed between the forwardmost elastic band and the remainder of the elastic bands and with subsequent forward sliding movement of the slide member 12 the elastic band to be discharged will be radially enlarged through passage over head 6 of magazine 4.

At the rear of the handle 2 are adjustment means which in the form shown is screw 20 which is threadedly received within the handle and serves to provide the rearward stop which limits rearward movement of slide member 12. When the slide member 12 is in this position, rotation of the pusher member 14 to the position shown in FIG. 1 will result in separation of a single forwardmost elastic band.

It is also noted that the slide member 12 has an upwardly projecting pusher pad 22 in order to facilitate forward movement of the slide member with respect to the handle 2. Also, the rear portion of the pusher member has a manually engageable sector 28 which is adapted to be depressed when it is desired to rotate the blade 18 upwardly.

Referring to FIG. 3, it is noted that the adjustment screw 20 is shown as separated for loading a magazine. The rear portion of slide 12 is shown projecting rearwardly out of the handle in spaced relationship with respect to the end of adjustment screw 20.

As is shown in FIGS. 1, 2 and 3, the forward portion of the handle 2 has a pair of upwardly projecting guide members 40, 42 which serve as both a stop to limit forward movement of the slide 12 and cooperate with guide walls 41, 43 to serve to define a channel for positioning of the magazine 4. Disposed forwardly of the stops 40, 42 is a tongue portion 44 which serves as a base to restrict downward deflection of the head portion 6 when the blade 18 is urging the same downwardly.

Also shown in FIG. 3 is a generally vertically oriented bore 46 in the handle within which a retainer hook of the magazine 4 will be secured.

Figure 14:
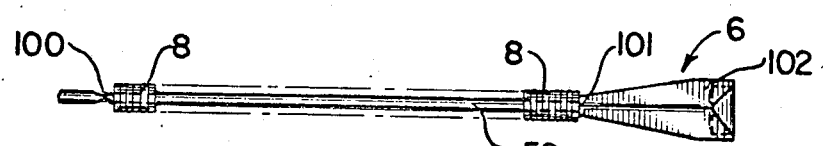
FIG. 14 is a top plan view of a form of magazine of the present invention.

Referring to FIGS. 4 and 14, it is seen that the magazine 4 has a guide rod 50 on which the elastic bands 8 are mounted. Depending downwardly from the rearward portion of the guide rod 50 is retainer hook 52 which is received within opening 46 of handle 2. In this manner, the magazine 4 is anchored to the apparatus.

Referring to FIGS. 4 and 4a, there is shown the pusher member 14 which has the manually engageable portion shown with a gripping surface 28 on the upper surface. In order to bias the pusher member 14 such that the blade 18 will normally be in the down position, first biasing means are provided in the form of wire spring 56 which tends to urge the manually engageable portion upwardly. If desired, other means such as a coil spring underlying gripping surface 28 could be employed in lieu of wire spring 56. Pushing downward on the gripping surface 28 will result in the rotation of the pushing member 14 so as to lift the blade 18. Still referring to FIG. 4, there is shown a plunger member 10 which is preferably a hollow inverted channel section with a tubular forward portion through which hook 52 passes. Rear section 62 and forward section 64 are separated by an enlarged spring stop member 65. The rear section 62 has a coil spring 66 positioned thereover tending to urge the plunger 10 forwardly. Spring 66 has a rear portion in contact with the closed rear wall of slide member 12 and a forward portion in contact with stop member 65. The forward section 64 has an elongated slot which is generally downwardly open and fits over the guide rod 50 and urges the overlying elastic bands 8 forwardly. In this manner, the spring will tend to urge the elastic bands 8 (not shown in this view) forwardly as the internal diameter of section 64 will generally approximate that of the elastic bands thereby maintaining the elastic bands in front of the plunger. Upwardly projecting tab 67 is adapted to be engaged by blade 18 of pusher member 14 in order to retract plunger 10 during reloading.

Referring to FIGS. 5, 6 and 7, it is seen that the handle has a rear portion 70 which in the form shown has greater height than either stop member 42 and interposed recess 72. As is shown in FIG. 6, a pair of sidewalls 74, 76 terminating in generally inwardly directed flanges define recess 78 in cooperation with base 80. Internal threads (not shown) are either formed within the rear portion 70 or are provided by a suitable insert in order to permit threaded engagement with screw 20. Referring to FIGS. 8 through 10, the plunger member is shown in greater detail. It is seen that the rear section 62 is an inverted channel over which the biasing means or spring 66 is positioned and restrained in part by stop member 65. The forward portion 64 is an inverted channel which has an open bottom or slot 90 in order to facilitate its passing over the guide rod 50 of the magazine 4. The forwardmost portion 92 is tubular in order to permit engagement with hook 52.

Figure 12:
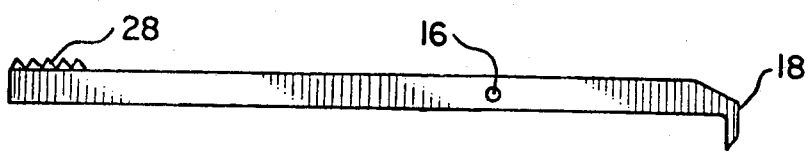
FIG. 12 is a front elevational view of the pusher of FIG. 11.
Figure 13:
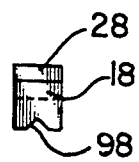
FIG. 13 is a left-hand elevational view of the pusher member of FIG. 14.

Referring to FIGS. 11 through 13, more specifically, certain additonal details of the pusher road will be considered. It is noted that the gripping portion 28 on its rear portion has greater height than the intermediate portion adjacent the pivot point 16. As is shown in FIG. 13 the lower portion of blade 18 has a recess 98 which converges upwardly. This permits the blade to have a self-centering action on the guide road as the surfaces which define the recess tend to act as pilot surfaces.

Figure 15:
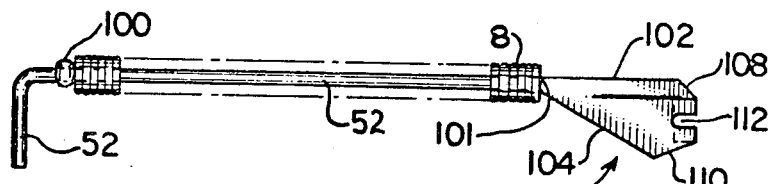
FIG. 15 is a front elevational view of the magazine of FIG. 14.
Figure 16:
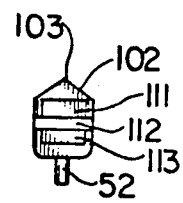
FIG. 16 is a left-hand elevational view of the magazine of FIG. 14.
Figure 17:
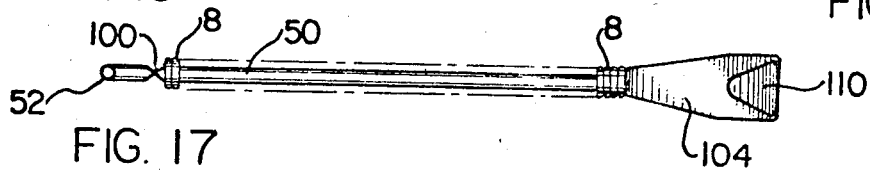
FIG. 17 is a bottom plan view of the magazine.

Referring now more specifically to FIGS. 14 through 16, further details of the magazine will be considered. The magazine has a guide rod 50 about which are secured a number of elastic bands 8. An enlarged or flattened portion 100 of the guide rod serves to restrict undesired rearward movement of the elastic bands. A rear portion of the head 101 is of sufficient transverse dimension as to resist undesired forward movement of the elastic bands. More specifically, the plunger 10 operating under the influence of spring 66 does not have adequate force to permit the forwardmost elastic band 8 to become enlarged and advance. The blade 18 of the pusher member 14 will enter between the forwardmost elastic band and the next preceding elastic band to thereby urge the elastic band 8 over the head in a manner to be described hereinafter.

The head 6 of the magazine has an upper surface 102 which diverges downwardly from apex 103. A lower surface 104 cooperates with the upper surface to define a forwardly diverging section of the head 6. Upper ramp 108 is a surface which slopes forwardly and downwardly and lower ramp 110 is a surface which slopes forwardly and upwardly. These two ramps 108, 110 serve to define a forwardly converging surface which is disposed forwardly of the forwardly diverging sector of the head 6. A face portion has a pair of transversely oriented recesses 111, 113 which are adapted to engage an orthodontic bracket and a transverse recess 112 of greater depth which is adapted to engage the transverse running arch wire. It will be appreciated that the head portion is so configured that the lower ramp surface 110 extends farther rearwardly than the upper ramp surface. As is shown in the right-hand portion of FIG. 4, an elastic band about to be discharged will be transciently supported by surfaces 104 and 108.

The head portion 6 depends downwardly such that a major portion of the head is disposed at a lower level than the axis of guide rod 50. Also, a horizontal plane passing through the center of recess 112 is such that the head will be asymmetrical with respect to such plane.

Figure 18:
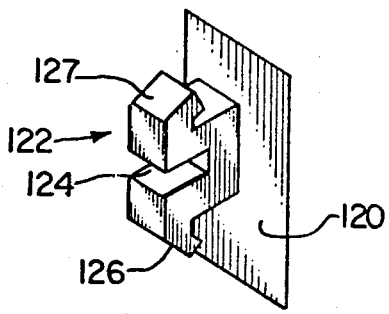
FIG. 18 shows schematically a perspective view of a dental bracket such as is used in orthodontics.
Figure 19:
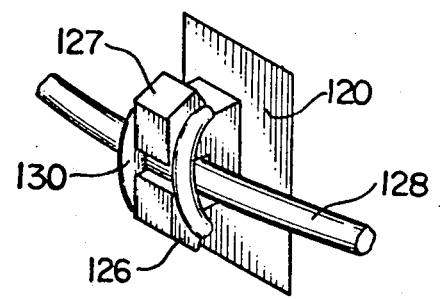
FIG. 19 shows the bracket of FIG. 16 with the wire and elastic band in place.

Referring to FIGS. 18 and 19, there is shown schematically, the surface of a band which has been wrapped around a tooth with the band being designated by the reference number 120. A winged bracket 122 has a pair of wings 126, 127 and a recess 124. An arch wire 128 passes through the recess 124 and is secured in position by the band 130 which is engaged with the two wings. In use of the tool of the present invention, the wing bracket would be received within recesses 111, 113 of the face and arch wire 128 would be received in recess 112 and then the band would be released. The device may also be employed with double brackets.

In FIGS. 20 through 22 details of the slide member 12 are shown. In creating the assembly, spring 66 (FIG. 4) is placed over rear portion 62 of plunger 10. The slide member 12 has tubular lower portion 134 defining bore 136. This subassembly may then be inserted into bore 136 defined by wall 134 of slide member 12 through the front opening. Rear portion 62 is introduced first. Then, as is shown in FIGS. 3, 5 and 6, this subassembly may be introduced into the rear of handle 2. The lower portion 134 (FIG. 21) of slide member 12 will be received within recess 78 and the upper portion of slide member 12 will project upwardly.

Figure 23:
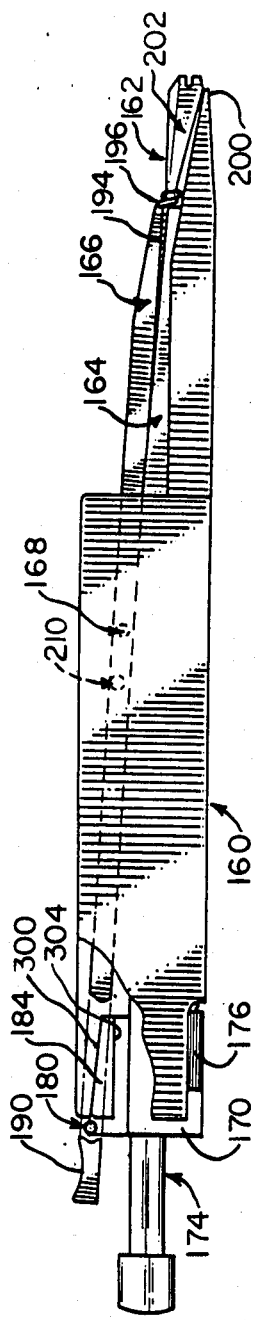
FIG. 23 is a front elevational view of another embodiment of the apparatus of the present invention.

Further embodiments of the invention are shown in FIGS. 23 and 51. It will be appreciated that in a general sense these may be operated by one hand much like one might operate certain types of retractable pens. The ligating devices can be held in the palm of the hand with the thumb resting on the slide extension 174 which protrudes from the rear end of the device.

The forward end of the device engages a bracket such as those shown in FIGS. 18 and 19 and then in a manner to be described hereinafter the elastic band is dispensed from the apparatus and secured on the bracket.

Figure 24:
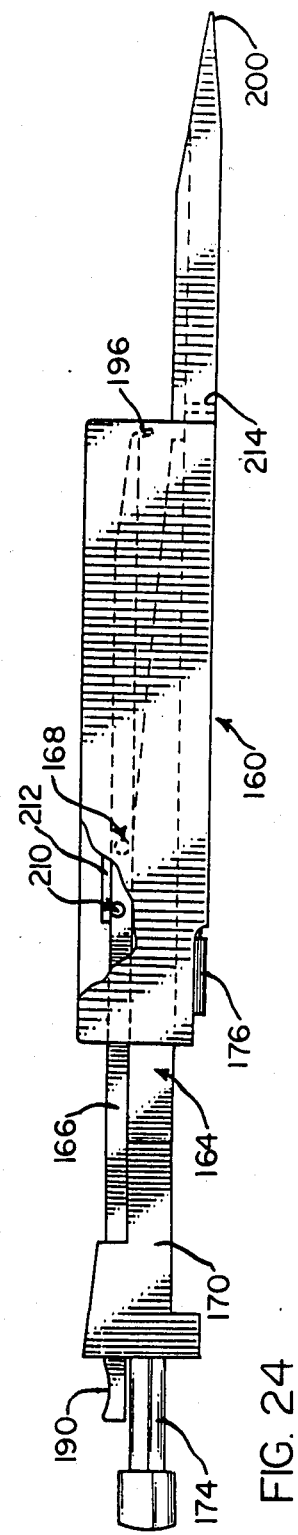
FIG. 24 is an elevational view showing a portion of the apparatus of FIG. 23 in a position suitable for loading a magazine.
Figure 25:
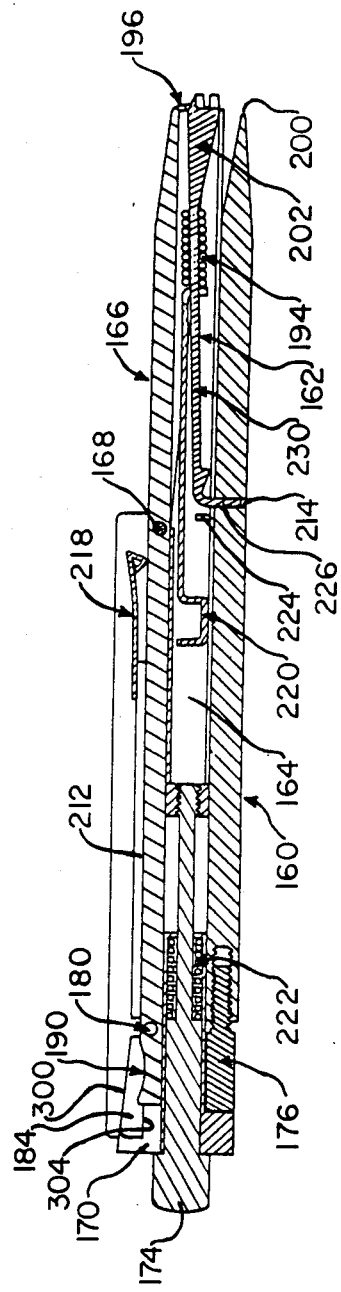
FIG. 25 is a cross-sectional view of the apparatus of FIG. 23.

Referring more specifically to the embodiment illustrated in FIGS. 23 through 25, it is seen that it has a handle 160 which has forwardly projecting portion terminating in a support spur 200. A magazine 162 has a rod 230 which terminates in a downwardly depending hook 226 which is received within opening 214 in the handle 160. A supply of elastic bands 194 is secured on the guide rod 230 intermediate the retainer hook 214 and the head portion 202.

As is shown in FIG. 25, a plunger 220 has a forwardly projecting portion which is adapted to advance the bands 194. A stop member 224 serves to limit the forward movement of the plunger 220. By holding the apparatus in a generally vertical orientation the follower 220 will slide downwardly and urge the elastic bands forwardly. If desired, a spring or other means may be provided in space 264 to urge follower 220 forwardly.

This embodiment employs a modified form of pusher member 166 which is shown in detail in FIGS. 29 and 30. In this embodiment, a rearwardly disposed finger engageable tab 190 is provided and forwardly thereof is a transversely projecting pin member 180 which functions as a cam follower. Pin member 210 is provided generally toward the middle of the pusher member 166. A pivot 168 about which the pusher member 166 pivots with respect to the slide 164 is also provided. At the forward end of the pusher member 166 is a blade 196 which extends generally downwardly and outwardly and has a recess 250.

Referring to FIGS. 26 through 28 some additional features of the handle 160 will be considered. It is noted that a pair of inwardly extending walls 212, 244 extend longitudinally, respectively, on the opposed walls 238, 240 which cooperate to define recess 236. Pin 210 on pusher member 166 is adapted to be received under these inwardly projecting walls as is shown in FIG. 24 to thereby control the position of the pusher member with respect to pivot 168. When pin 210 is in underlying relationship with respect to walls 212, 244, the pusher member will be in a generally horizontal position. When the pin 210 moves forwardly beyond walls 212, 244 pivoting is permitted to thereby permit the pusher member to assume the orientation shown in FIG. 23. Leaf spring 218 (FIG. 25) which is secured within slots 242 and the second opposed slot (not shown) by means of tabs 316, 318 (FIGS. 40 and 41) causes a spring force to be applied in a downwardly direction against the pusher member by portion 320. If desired, other spring means such as a wire spring or integrally molded protrusions could be employed in lieu of leaf spring 218. Web 232 has a threaded bore 234.

Referring once again to FIGS. 23 through 25, a cycle of operation will be considered. With the blade 196 positioned behind the forwardmost elastic band as is shown in FIG. 23, depressing the slide extension 174 by urging it forwardly will cause the pusher member to move forwardly thereby urging the elastic band over the enlarged head 202 to express the elastic band from the apparatus. During this process, the trailing edge of the elastic band slides along diverging surface 338 (FIG. 45) of the magazine head 202. As the slide member 164 advances the magazine will be caused to pivot upward such that the head 202 which initially is shown resting on the support spur 200 (FIG. 23) will be elevated to the position shown in FIG. 25.

In the form illustrated, it will be appreciated that the slide extension 174 is threadedly secured to the rear portion of slide 164. Threaded member 176 serves to permit adjustment between the handle stop member 170 and the head of the slide extension 174 to permit adjustment of the limit of forward travel of the slide extension 174. Spring 222 urges the slide extension 174 rearwardly to assume its normal position shown in FIG. 23.

Considering the cycle of operation with continued reference to FIGS. 23 through 25, it will be appreciated that cam follower or pin 180 is affixed to the rear of the pusher member 166 and rides along the upper surface 300 of cam 184 thus preventing the blade 196 from rotating upwardly. This cam 184 is so configured as to work in combination with the flex in the pusher member in order to exert pressure on the blade to assure that the elastic band cannot escape between the advancing blade and the upper surfaces 102 of the magazine head 202. At this stage, the radial force on the blade is transferred through the magazine head 202 and cancelled by the rigid support spur 200 thus preventing excessive outward deflection of the magazine 162.

By continued forwardly applied force on the slide extension 174, the user continues to advance the blade 196 thereby causing the forwardmost elastic band to stretch progressively. Before the trailing edge of the band comes in contact with the rigid support spur 200, the front edges of the slide 164 make contact with the magazine head 202 at a point behind the elastic band. Continued forward movement of the slide lifts the magazine head 202 away from the support spur 200 thereby providing a gap for the elastic band to pass through. At this point the slide cancels the radial force exerted by the blade. As the user continues to advance the blade, the blade rides forward over the forward release ridge 330 (FIG. 45), slides inward along the forward ramp 334 and diverging surface 338 of the magazine head 202 and contracts under the tie wings of the brackets. The front end of the slide 164 ould be employed to assist with urging the elastic bands forwardly. Soon after this has been accomplished, the cam follower 180 passes over the forward edge of the cam 184. In a preferred form, upper surface 300 of the cam will have an upwardly open notch of sufficient size to receive cam follower 180 to permit the elastic band to be discharged before the blade 196 passes the point at which it no longer rests on the magazine. This dwell action permits tool removal from tooth contact before the forwardmost blade position is attained. Continued forward pressure on the slide extension 174 will permit farther forward movement of the blade 196. As it is now free to rotate, the blade 196 moves radially upwardly and away from the magazine head 202. This motion is accomplished by the pressure of the leaf spring 218 (FIG. 25) which is now exerting a force on the pusher member 166 at a point behind pivot 168. An audible click may be heard as the pusher member is snapped into its new position thereby telling the user that the installation of a single ligature has been completed.

At this point the user releases pressure on the slide extension 174. The compression spring 222 withdraws the slide assembly to its starting position. The cam follower 180 slides along the lower surface 304 of the cam 184. This maintains the blade's position above and away from the magazine head 202 and allows it to clear the stack of elastic bands. When the cam follower 180 passes over the cam's rear edge pressure from leaf spring 218 which is now in a position in front of pivot 168 rotates the pusher member 166 thereby forcing the blade between the two elastic bands which are next in line. The cycle is complete and the next elastic band is ready to be pushed forward by the blade for application to the next bracket.

In the form illustrated, the cam 184 is supported on cam housing 170 which has a central bore through which slide extension 174 passes.

During this cyclic process, the stack of elastic bands 194 may be advanced in any suitable manner. In the embodiment shown in FIG. 25, the plunger 220 has sufficient weight to advance the elastic bands 194 when the apparatus is held in a vertical position. In the embodiment illustrated in FIG. 51, the plunger 220 is advanced by the action of compression spring 446. The plunger and spring are guided by a rod 448 whose head 458 limits the forward travel. In both instances, the stack of elastic bands is held against alignment tabs 326 (FIGS. 42 and 43) on the magazine head 202. This assures that the next band will be accurately aligned with the blade 196 and is properly positioned for dispensing.

Loading of a magazine into the apparatus will be described with reference to FIG. 24. In the position shown, the apparatus is ready to receive a full magazine. In order to achieve this open position, the user depresses the finger tab 190 on the rear of the pusher member 166 and retracts the slide assembly 164, cam housing 170 and compression spring 222 by pulling on slide extension 174. A pin 210 located behind pivot 168 on pusher member 166 engages under and slides along walls 212, 244 thereby preventing the blade from rotating downwardly. A tab 224 located on slide 164 retracts the plunger 220.

A new magazine 162 is then installed by inserting its hook member 226 into the hole 214 in the handle. The user then replaces the slide assembly allowing the blade 196 to pass over the stack of elastic bands 194. The calibration screw 176 can now be adjusted until the blade 196 is properly aligned with the rear surface of the first elastic band. Calibration accommodates elastic bands of different thickness and compensates for difference in manufacturing tolerances and wear. After calibration, the ligating device is again ready for use.

Several additional features of the embodiment of FIGS. 23 through 25 will now be considered. As is shown in FIGS. 26 through 28, the handle 160 has a base wall 232, a pair of sidewalls 238, 240 and a pair of inwardly projecting tabs 246, 248 which are adapted to engage the channels on the slide in order that they, in turn, are in intimate engagement with the magazine head.

FIGS. 31 and 32 show details of the slide member including the threaded recess 262 within which the forward portion of the slide extension 174 is received. Within the forward portion of the slide is shown a pair of opposed bottom waLLs 254, 256 with an interposed slot 266 which allows the slide to pass over the magazine hook 226 and sidewall extensions 258, 260. A pair of sidewalls 264 (one not shown) underlie extensions 258, 260.

FIGS. 37 through 39 illustrate the cam housing guide which supports the cam supports 184, 298 which has cam surfaces 300, 302, 304 and 306 and permits interengagement with the cam follower and the slide for movement therewith. Cam 184 is supported on member 170 which defines tubular portion 308 having forward end 310 and base portion 312.

A detail of the slide extension 174 is shown in FIG. 34 which shows the rear knob portion 268, the intermediate portion 269 and the rod portion 270 which terminates in threaded end 272.

FIGS. 35 and 36 show the plunger 220 which in the form shown has a rear generally upwardly open channel 274, an upwardly open channel 278, and a downwardly projecting forward portion 276 having recess 296 which is adapted to engage the magazine rod 230 to urge the rubber band array forwardly.

The details of the magazine are shown in FIGS. 42 through 44 wherein a downwardly depending hook 226 is provided at the rear, an enlargement 324 to limit rearward movement of the array of elastic bands 194 on rod 230 is provided and a forward stop 326 is provided. The head provides upper surfaces 328, 332, an apex 330, a downwardly diverging surface 338 and a forwardly converging portion defined by surfaces 334, 340. A forwardly open recess 344, 348 is provided in the forward portion 342 of the head 342.

FIG. 45 shows a modified form of magazine head wherein the recess is generally angularly downwardly open.

FIG. 46 through 49 show further alternate embodiments of magazine heads. In the embodiment of FIG. 46, the rod 360 terminates in a head which has series of generally planar surfaces 361, 362, 366 and a similar surface 364 generally similar in shape to surface 362. A recess is defined by the forward portions of these walls and wall 368. A notch is provided at 370 and a further notch at 372. FIG. 47 shows a structure similar to FIG. 46 except that there is no lower wall and no rear wall. Rod 380 cooperates with surfaces 382, 384 and a further wall which bears notch 386. Notch 388 is provided in wall 384.

FIG. 48 illustrates a generally tapered wall 394 which is secured to rod 390 and has a rear wall 396 cooperating with annular wall 392 to define a recess.

FIG. 49 illustrates a rod 400, a pair of converging upper surfaces 402, 404, a pair of converging lower surfaces, 406, 408.

The magazine of FIGS. 53 through 55 contains recesses 465, 466 in the walls to permit ready finger engagement. The magazine has a rod 162 and a head 202, a body portion 462 with a pair of slots 463, 464 generally upwardly open and a tubular portion 461. Slots 463, 464 provide clearance for plunger movement.

The embodiment shown in FIG. 51 has a pusher member 166 with a blade 196 and a pivot 168 with a spring 218 functioning as in the earlier embodiment. A cam follower 210 (shown schematically) cooperates with cam 184 which has upper surface 300 and lower surface 304. A slide extension 174 which has extension 450 is urged forwardly in order to advance and raise the blade 196 of pusher member 166. The magazine which is shown in FIGS. 53 through 55 is installed by guiding it over the slide 164 and support spur 200 until it clicks into place in recess 460 between tabs 438, 442 on retainer clip 434. Once the user releases pressure on the slide extension 174, the blade 196 will retract and drop into place behind the first elastic band. Depressing the tab 442 on the retainer clip 434 frees the magazine for removal. It will be appreciated that the spur 200 enters into the bore 461 of the magazine during insertion and removal.

The embodiment of FIG. 51 shows another means of calibration. By loosening the screw 456 the user can change the position of the retaining clip 434 and magazine 162 thereby adjusting the alignment between the blade 196 and the stack of elastic bands. This method allows the cam 184 and spring stop 452 to be an integral part of the handle 10. This is illustrated in FIGS. 56 through 58.

As is shown in FIGS. 59 and 60, the pusher member, in this embodiment, while having a pivot 168 and a cam follower or pin 180 does not require the use of the additional pin 210.

Also, the slide as shown in FIGS. 61 and 62 does not have to be slotted, but does have openings 496, 498 to accept the slide extension. It has sidewalls 492, 494, a forward edge 430 and base 500.

FIG. 64 shows the slide extension of this embodiment wherein a peg 450 serves to assist with retention of spring 222 and downwardly projecting rivets 490, 491 are adapted to be received within openings 496, 498, respectively, of the slide. The rear surface of the slide extension 174 has been indicated by the reference number 268.

FIGS. 66 and 67 show the clip member 434 which has an elongated opening 502 for receiving screw 456.

The plunger is shown in FIGS. 68 and 69 and is indicated generally by the reference number 220. The rear portion has depending flange 504 which receives rod 448 and the forward portion is bifurcated at 276 with recess 296. Recess 278 is provided in order to permit clearance over the adjacent components.

The method of the present invention involves providing apparatus which is preferably generally of the above-described type and inserting behind the forwardmost elastic band a blade portion of a pusher member which is pivotally mounted on a slide member. Moving the slide member forwardly urges the elastic band through contact with the blade onto the head portion of the magazine and the enlarged band will be discharged therefrom. For orthodontic uses, effective interengagement between the face of the head and the orthodontic bracket will be accomplished first.

While for convenience of reference and clarity of disclosure herein, reference has been made to particular directions such as "forward", "rearward", "upper", "lower" and words of similar import, it will be appreciated that these words are used in order to establish the relative relationships between the parts and are not to be indicative of any limitation in respect of angle at which a tool should be held in actual use.

While for convenience of reference herein the system has been disclosed as selecting a single elastic band for discharge with the subsequent bands being discharged sequentially, if desired, the instrument may be set so as to discharge two or more elastic bands simultaneously.

While reference herein has been made to use in connection with orthodontic appliances, it will be appreciated that the invention is not so limited and a wide variety of medical, industrial and other uses will be apparent to those skilled in the art.

It will be appreciated that while a specific single width of band has been illustrated for clarity of disclosure, the system is adapted for use with a wide variety of band widths. All that is required is a suitable adjustment to stop means such as screw 20.

Whereas particular embodiments of the invention have been described for purposes of illustration, it will be evident to those skilled in the art that numerous variations of the details may be made without departing from the invention as defined in the appended claims.

We claim:

1. Apparatus for dispensing elastic bands comprising an elongated handle member,
   a slide member secured for relative longitudinal sliding movement with respect to said handle,
   a magazine of said elastic bands secured to said handle and adapted for generally forward discharge of said elastic bands, pusher means for sequentially separating elastic bands and causing them to be dispensed from a forward portion of said magazine, said pusher means being pivotally mounted on said slide member, said pusher means being mounted for relative sliding movement with respect to said magazine, whereby said pusher means may be indexed with respect to the next said elastic band to be dispensed, first biasing means operatively associated with said pusher means for urging said pusher means into elastic band engaging position, and second biasing means operatively associated with said magazine for urging said elastic bands forwardly.

2. The dispensing apparatus of claim 1 including said pusher member having a rearwardly disposed manually engageable portion and a forwardly disposed elastic band engaging blade 3. The dispensing apparatus of claim 2 including said pusher member being pivoted about an axis disposed intermediate said manually engageable portion and said blade.

4. The dispensing apparatus of claim 3 including said first biasing means having spring means underlying said pusher member for urging the rear portion of said pusher means generally away from said slide member.

5. The dispensing apparatus of claim 2 including stop means for limiting the forward movement of said elastic bands under the influence of said second biasing means.

6. The dispensing apparatus of claim 5 including said second biasing means having a plunger member in engagement with said elastic bands and spring means urging said plunger forwardly.

7. The dispensing apparatus of claim 6 including said magazine having a guide rod with a plurality of elastic bands secured thereon, and said plunger member in contact with a rearwardly positioned elastic band.

8. The dispensing apparatus of claim 7 including adjustable stop means for limiting rearward travel of said slide member, and said blade of said pusher member adapted to separate a said elastic band from the remaining bands when said slide member is in contact with said adjustable stop means.

9. The dispensing apparatus of claim 8 including said adjustable stop means being a screw.

10. The dispensing apparatus of claim 8 including said magazine having a forwardly disposed forwardly diverging head portion.

11. The dispensing apparatus of claim 10 including a forwardly converging head portion disposed forwardly of said forwardly diverging head portion.

12. The dispensing apparatus of claim 1 including a forward portion of said head being non-adjustable and having a contour adapted to engage an orthodontic bracket.

13. The dispensing apparatus of claim 12 including said forward contour including a generally horizontally oriented forwardly open recess.

14. The dispensing apparatus of claim 13 including said head having an asymmetrical shape with respect to a horizontal plane passing through the center of said recess.

15. The dispensing apparatus of claim 12 including the rear portion of said head having elastic band stop means for resisting forward movement of said elastic bands therebeyond solely under the influence of said plunger member.

16. The dispensing apparatus of claim 15 including a rear portion of said magazine having a downwardly depending retainer means, and said handle having an opening receiving said retainer means.

17. The dispensing apparatus of claim 15 including said slide means having a generally upwardly projecting push tab disposed rearwardly of said pusher member.

18. The dispensing apparatus of claim 11 including said magazine head forwardly converging portion having an upper ramp surface sloping generally forwardly and downwardly and a lower ramp surface sloping generally forwardly and upwardly.

19. The dispensing apparatus of claim 18 including said lower ramp surface extending farther rearwardly than said upper ramp surface.

20. The dispensing apparatus of claim 18 including said handle having a forwardly disposed tongue underlying said magazine head to resist excessive deflection of said head.

21. The dispensing apparatus of claim 20 including said forwardly diverging portion have a generally downwardly and forwardly extending support surface, and a said elastic band being secured on said support surface and said forward ramp prior to discharge.

22. The dispensing apparatus of claim 7 including said plunger means having a forward portion disposed in partially surrounded relationship with respect to said magazine guide rod and disposed rearwardly of said elastic bands.

23. The dispensing apparatus of claim 22 including said handle having upwardly projecting stop means for limiting forward movement of said slide member.

24. The dispensing apparatus of claim 1 including said pusher member having cam follower means disposed adjacent to said manually engageable portion.

25. The dispensing apparatus of claim 24 including cam means secured to said assembly at or adjacent a rearward portion of said assembly, whereby reciprocating movement of said slide member will cause said cam follower to move along said cam means and cause said pusher means to rotate about its pivotal attachment to said slide member.

26. The dispensing apparatus of claim 25 including said cam means being so configuarated and said pusher means being so positioned that movement of said slide member during a cycle of operation of said apparatus will cause said cam follower to move around the outer surface of said cam means.

27. The dispensing apparatus of claim 26 including said first biasing means also serving to urge said pusher means out of elastic band engaging position.

28. The dispensing apparatus of claim 26 including rod means projecting from said pusher means, and said handle member having transversely inwardly directed walls for receiving said rod means thereunder to control rotational movement of said pusher member during a portion of the translational movement of said slide member.

29. The dispensing apparatus of claim 26 including slide extension means operatively associated with said slide member and projecting rearwardly.

30. The dispensing apparatus of claim 29 including said cam means disposed rearwardly of said slide member and having a bore therethrough, and
said slide extension passing through said bore, whereby a force applied forwardly to said slide extension will urge said slide member and said cam means forwardly.

31. The dispensing apparatus of claim 30 including second biasing means for urging said elastic bands forwardly, and
said second biasing means having a follower member.

32. The dispensing apparatus of claim 31 including adjustment means for adjusting the relative positions of said handle member and said cam member.

33. The dispensing apparatus of claim 32 including coil spring means for urging said slide member extension rearwardly.

34. The dispensing apparatus of claim 27 including said first biasing means being spring means secured to said handle member.

35. The dispensing apparatus of claim 25 including said cam means secured to said handle member.

36. The dispensing apparatus of claim 35 including clip means secured to said handle member for securing said magazine to said handle.

37. The dispensing apparatus of claim 36 including means for adjusting the position of said clip means with respect to said handle.

38. The dispensing apparatus of claim 37 including said cam means being spaced from said slide extension means.

39. The dispensing apparatus of claim 37 including said second biasing means having coil spring means.

40. A method of delivering elastic bands comprising a magazine of said elastic bands having a guide rod on which said bands are disposed, a head portion having a forwardly diverging portion disposed rearwardly of a forwardly converging head portion and an orthodontic bracket engaging front face,
inserting behind the forwardmost said elastic band, a blade portion of a pusher rod which is mounted on a slide member,
moving said slide member forwardly to urge said elastic band onto said head with a portion of said elastic band being on the diverging portion of said head and a portion being on the converging portion of said head,
continuing said forward movement of said slide to discharge said elastic band,
providing said blade member on a pusher member which is rotatably secured to said slide member, and
relatively positioning said slide member in contact with a stop member prior to inserting said blade behind said elastic band, whereby rotation of said pusher member will effect insertion of said blade at the desired position with respect to said elastic band.

41. The method of claim 40 including prior to discharging said elastic band establishing contact between said head face and said orthodontic bracket, whereby contact and alignment are maintained between said head face and said orthodontic bracket by direct manual control pressure.

42. The method of claim 41 effecting said blade insertion solely on the upper portion of said guide rod.

43. The method of claim 42, whereby rotation of said pusher member results from cam follower means riding on cam means.

* * * * *